(12) United States Patent
Nishiie et al.

(10) Patent No.: US 9,895,051 B2
(45) Date of Patent: Feb. 20, 2018

(54) ASSIST TOOL, INSERTION APPARATUS TO WHICH THE ASSIST TOOL IS ATTACHED, AND INTRODUCTION APPARATUS INCLUDING THEM

(71) Applicant: OLYMPUS CORPORATION, Tokyo (JP)

(72) Inventors: Takehiro Nishiie, Akishima (JP); Robert E. Ailinger, Norwood, MA (US); James J. Frassica, Chelmsford, MA (US); Richard M. Andrews, Lincoln, RI (US); David E. Gately, Maynard, MA (US); Matthew S. Carlone, Marlborough, MA (US)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/362,942

(22) Filed: Nov. 29, 2016

(65) Prior Publication Data

US 2017/0071447 A1  Mar. 16, 2017

Related U.S. Application Data (63) Continuation of application No. PCT/JP2015/079600, filed on Oct. 20, 2015.

(Continued)

(51) Int. Cl.
*A61B 1/005* (2006.01)
*A61B 1/00* (2006.01)
(Continued)

(52) U.S. Cl.
CPC .......... *A61B 1/005* (2013.01); *A61B 1/00071* (2013.01); *A61B 1/00112* (2013.01);
(Continued)

(58) Field of Classification Search
CPC . A61B 1/005; A61B 1/00071; A61B 1/00165; A61B 1/06; A61B 1/00112;
(Continued)

(56) References Cited

U.S. PATENT DOCUMENTS

| | | | |
|---|---|---|---|
| 6,589,164 B1 * | 7/2003 | Flaherty | A61M 25/0017 600/121 |
| 8,574,220 B2 * | 11/2013 | Frassica | A61M 25/0017 600/137 |

(Continued)

FOREIGN PATENT DOCUMENTS

| | | |
|---|---|---|
| CN | 201591540 U | 9/2010 |
| CN | 102933254 A | 2/2013 |
| CN | 103284678 A | 9/2013 |
| JP | 2014-524807 A | 9/2014 |

OTHER PUBLICATIONS

International Search Report dated Jan. 19, 2016 issued in PCT/JP2015/079600.

(Continued)

*Primary Examiner* — Timothy J Neal
(74) *Attorney, Agent, or Firm* — Scully, Scott, Murphy & Presser, P.C.

(57) ABSTRACT

An assist tool attachable to an insertion section of an insertion apparatus includes a tube including a longitudinal axis. The tube is provided with a lumen through which the insertion section is insertable. The tool includes a connecting mechanism. The connecting mechanism receives a drive force and is rotated together with the tube with respect to the insertion section inserted through the lumen. The tool includes a locking mechanism provided on a more distal end side than the connecting mechanism in the tube. The locking mechanism includes a convex portion or a concave portion engaged with the insertion section to restrict movement of the tube along the longitudinal axis with respect to the insertion section. Furthermore, an insertion apparatus to which the tool is attached and an introduction apparatus including them is provided.

10 Claims, 11 Drawing Sheets

Related U.S. Application Data (60) Provisional application No. 62/096,571, filed on Dec. 24, 2014.

(51) Int. Cl.
*A61B 1/06* (2006.01)
*A61B 1/01* (2006.01)
*A61B 1/04* (2006.01)

(52) U.S. Cl.
CPC ............ *A61B 1/00165* (2013.01); *A61B 1/01* (2013.01); *A61B 1/06* (2013.01)

(58) Field of Classification Search
CPC ............ A61B 1/00133; A61B 1/00135; A61B 1/00154; A61B 1/00156
See application file for complete search history.

(56) References Cited

U.S. PATENT DOCUMENTS

2010/0298642 A1\* 11/2010 Trusty ................ A61B 1/00135
600/114
2012/0029281 A1 2/2012 Frassica et al.

OTHER PUBLICATIONS

Chinese Office Action dated Jul. 17, 2017 in Chinese Patent Application No. 201580022203.3.
English translation of International Preliminary Report on Patentability dated Jul. 6, 2017 together with the Written Opinion received in related International Application No. PCT/JP2015/079600.

\* cited by examiner

ASSIST TOOL, INSERTION APPARATUS TO WHICH THE ASSIST TOOL IS ATTACHED, AND INTRODUCTION APPARATUS INCLUDING THEM

CROSS-REFERENCE TO RELATED APPLICATIONS

This application is a Continuation Application of PCT Application No. PCT/JP2015/079600, filed Oct. 20, 2015 and based upon and claiming the benefit of priority from U.S. Provisional Application No. 62/096,571, filed Dec. 24, 2014, the entire contents of all of which are incorporated herein by references.

BACKGROUND OF THE INVENTION

1. Field of the Invention

The present invention relates to an assist tool attachable to an insertion section of an insertion apparatus, an insertion apparatus to which the assist tool is attached, and an introduction apparatus including them.

2. Description of the Related Art

An assist tool to be attached to an insertion apparatus, for example, an insertion section of an endoscope is known. The assist tool assists insertion of the insertion section into a body cavity. For example, US2012/0029281 discloses an apparatus for accessing a bodily passageway, the apparatus comprising an endoscope including an insertion section, and a rotation unit including a disposable drive tube attached to an external circumferential surface of the insertion section. A spiral fin is provided on an external circumferential surface of the drive tube. In the endoscope, a drive unit is provided to transmit a drive force to the rotation unit. Furthermore, a plurality of rollers abutting against the drive unit is provided on an internal circumferential surface of the drive tube.

In the apparatus, when the rotation unit is attached to the insertion section of the endoscope, the drive tube is rotated around a central axis thereof by a drive force transmitted from the drive unit to the drive tube via the rollers. For example, when the apparatus is used for inspection, diagnosis, or treatment of a serpentine long organ, such as the small intestine and the large intestine, the insertion section of the endoscope advances into deep distal sites, while pressing the wall abutting against the spiral fin of the rotating drive tube, such as the small intestinal wall and the large intestinal wall, toward the proximal end.

BRIEF SUMMARY OF THE INVENTION

According to one embodiment of the invention, an assist tool attachable to an insertion section of an insertion apparatus comprises a tube including a distal end portion and a proximal end portion, the tube including a longitudinal axis extending from the distal end portion to the proximal end portion, the tube being provided with a lumen through which the insertion section is insertable, a connecting mechanism provided in the tube, the connecting mechanism receiving a drive force and being rotated together with the tube with respect to the insertion section inserted through the lumen, and a locking mechanism provided on a more distal end side than the connecting mechanism in the tube, the locking mechanism including a convex portion or a concave portion to be engaged with the insertion section to restrict movement of the tube along the longitudinal axis with respect to the insertion section.

According to other embodiment of the invention, an insertion apparatus to which the above-mentioned assist tool is attached comprises a concave portion or a convex portion extending along an external circumferential surface of the insertion section and fitted with the convex portion or the concave portion of the assist tool such that the convex portion or the concave portion of the assist tool moves along the external circumferential surface of the insertion section with rotation of the tube.

According to other embodiment of the invention, an introduction apparatus comprises the above-mentioned assist tool and the insertion apparatus including a concave portion or a convex portion extending along an external circumferential surface of the insertion section, the concave portion or the convex portion of the insertion apparatus slidably fitted with the convex portion or the concave portion of the assist tool such that the convex portion or the concave portion of the assist tool moves along the external circumferential surface of the insertion section with rotation of the tube.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be explained hereinafter with reference to drawings.

Figure 1:
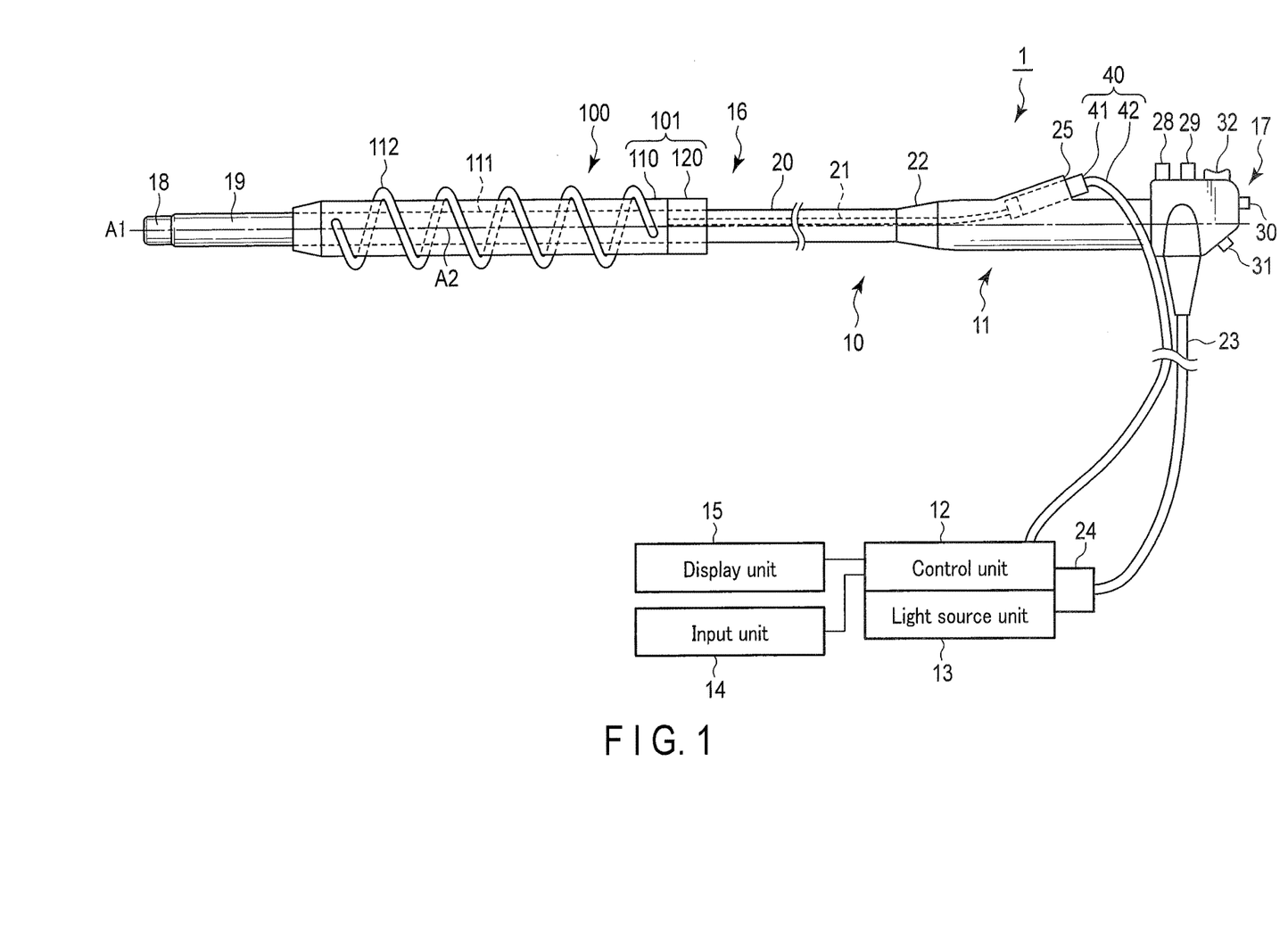
FIG. 1 is a diagram schematically illustrating an endoscope apparatus according to an embodiment of the present invention, that is, an endoscope and a rotation unit attachable thereto.

FIG. 1 is a diagram schematically illustrating an endoscope apparatus 1 being introduction apparatus according to an embodiment of the present invention. The endoscope apparatus 1 includes an endoscope system 10 including an endoscope 11 being an insertion apparatus, and a rotation unit 100 being an assist tool attachable thereto.

First, the endoscope system 10 will be explained hereinafter. The endoscope system 10 includes the endoscope 11, a control unit 12, a light source unit 13, an input unit 14, and a display unit 15.

The endoscope 11 includes an elongated insertion section 16, and an operation section 17 provided on a proximal end side of the insertion section 16. The insertion section 16 has a long tube-shaped member disposed on a distal end side of the endoscope. The insertion section 16 includes a distal rigid portion 18, a bending portion 19 provided on the proximal end side of the distal rigid portion 18, and a flexible tube portion 20 provided on the proximal end side of the bending portion 19. The distal rigid portion 18 includes an illumination optical system, an observation optical system, and an image sensor and the like that are not illustrated. The bending portion 19 is bent in a desired direction by a user's operation of the operation section 17. The flexible tube portion 20 is bendable, and bent to follow the bending shape in the body cavity into which the insertion section 16 is inserted, for example. A channel 21 extends inside the insertion section 16, to insert a drive shaft 51 of a drive unit 50 described later therethrough.

The operation section 17 is coupled with the flexible tube portion 20 via a stopper 22. An illumination light fiber and an electrical wire and the like are arranged from inside of the insertion section 16 to the inside of the operation section 17. The illumination light fiber has a distal end connected with the illumination optical system of the distal rigid portion 18. The electrical wire has a distal end connected with the image sensor of the distal rigid portion 18. The fiber and the electrical wire are contained in a universal cable 23 extending from the proximal end side of the operation section 17. A scope connector 24 is provided at a proximal end of the universal cable 23. The universal cable 23 is connected with the control unit 12 and the light source unit 13 via the scope connector 24. A drive source attachment port 25 is provided on the operation section 17, the drive source attachment port 25 communicating with the channel 21 located inside the insertion section 16.

The control unit 12 is electrically connected with the endoscope 11, the light source unit 13, the input unit 14, and the display unit 15. The control unit 12 controls operations of the endoscope 11 and peripheral devices (such as the light source unit 13 and a drive source 40 described later) connected thereto. The control unit 12 also includes an image processing unit that is not illustrated. The light source unit 13 supplies illumination light to the illumination optical system arranged in the distal end rigid 18 via the illumination light fiber. The input unit 14 is an ordinary input unit such as a keyboard and a mouse, and used for the user's inputting various instructions to the endoscope 11 or the like. The display unit 15 is an ordinary display unit such as a liquid crystal display, to display images acquired by the image sensor of the distal rigid portion 18 and subjected to image processing by the control unit 12, and operating information.

Figure 2:
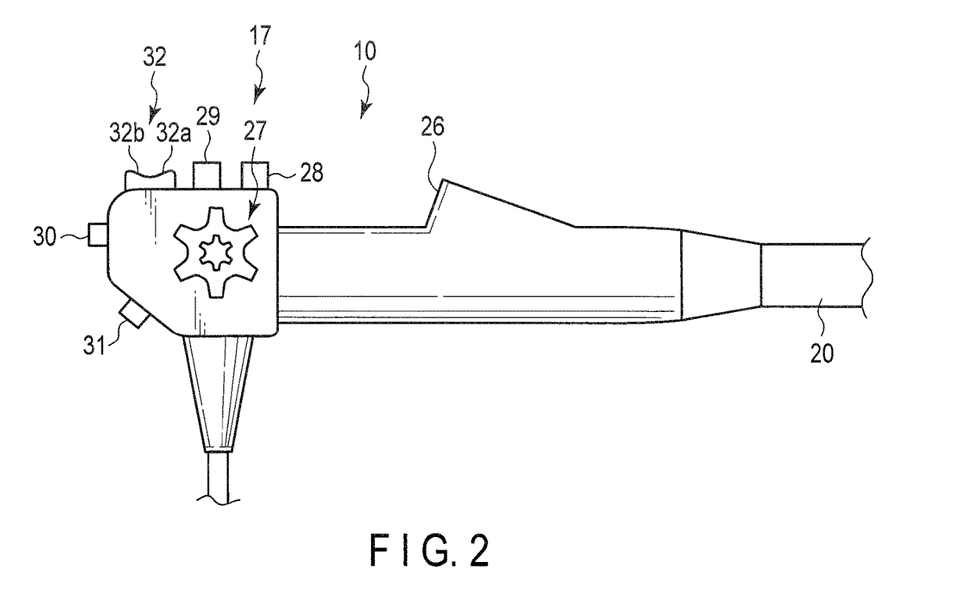
FIG. 2 is a diagram illustrating a side surface on a reverse side of an operation section of the endoscope illustrated in FIG. 1.

FIG. 2 is a diagram illustrating a side surface on a reverse side of the operation section 17 of the endoscope 11 illustrated in FIG. 1. The operation section 17 includes a treatment tool insertion port 26 communicating with a treatment tool channel (not illustrated) extending inside the insertion section 16. The treatment tool insertion port 26 is arranged side by side with the drive source attachment port 25 illustrated in FIG. 1. A treatment tool, such as an ultrasonic probe and biopsy forceps is inserted into the treatment tool insertion port 26.

As illustrated in FIG. 2, the side surface of the operation section 17 is provided with a bending operation knob 27 to receive an input of an operation to bend the bending portion 19 in a desired direction. Inside the operation section 17, a proximal end of a bending wire (not illustrated) to bend the bending portion 19 is connected with a shaft coupled with the bending operation knob 27. The distal end of the bending wire is connected with the distal end portion of the bending portion 19. When the user rotates the bending operation knob 27, the bending wire coupled therewith is pulled, and thereby the bending portion 19 is bent.

The operation section 17 is provided with various types of switches 28, 29, 30, and 31, such as an air/water feed switch, a suction switch, an imaging switch, and another changeover switch to change over a predetermined function. The operation section 17 is also provided with a rotating operation input switch 32 to output a signal for rotating the rotation unit 100 around a central axis A1 of the insertion section 16 to the control unit 12. When the user presses a position indicated with a reference numeral 32a, for example, to incline the switch 32, the rotation operation input switch 32 outputs a signal to rotate the rotation unit 100 in a first direction (for example, a clockwise direction) to the control unit 12. When the user presses a position indicated with a reference numeral 32b to incline the switch 32, the rotation operation unit switch 32 outputs a signal to rotate the rotation unit 100 in a second direction (for example, a counterclockwise direction) opposite to the first direction to the control unit 12.

With reference to FIG. 1 again, a drive source 40 to rotation-drive the rotation unit 100 around the central axis A1 is attached to the drive source attachment port 25. The drive source 40 includes a motor main body 41 including a rotary shaft, and a motor cable 42 extending from the motor main body 41. The external circumference of the motor main body 41 is held on the drive source attachment port 25 with a holder ring that is not illustrated. The rotary shaft of the motor main body 41 is connected with the drive shaft 51 of the drive unit 50 described later. The proximal end of the motor cable 42 is electrically connected with the control unit 12.

Next, the rotation unit 100 will be explained. The rotation unit 100 includes a rotatable tube 101, the rotatable tube 101 including a cylindrical tube main body 110 and a connector 120 provided on the proximal end side of the tube main body 110. The tube 101 is a disposal tube that is detachably attached onto the external circumferential surface of the insertion section 16. The connector 120 is provided to attach the tube 101 at its proximal end side onto the insertion section 16.

The tube 101 includes a distal end portion and a proximal end portion, and includes a longitudinal axis A2 extending from the distal end portion to the proximal end portion. When the tube 101 is attached onto the insertion section 16, the longitudinal axis A2 is coaxial with the rotation central axis A1 described above. The tube 101 is provided with a lumen 111, through which the insertion section 16 can be inserted, over the whole length of the tube 101. The internal circumferential surface forming the lumen 111 has a shape that is substantially fitted on the shape of the external circumferential surface of the insertion section 16 when the tube 101 is attached onto the insertion section 16.

The tube main body 110 is a flexible tube including a corrugated external surface. The tube main body 110 is made of a resin material such as polyurethane. At least part of the external circumferential surface of the tube main body 110 is provided with a spiral fin 112 that is provided in a clockwise spiral manner as viewed from the proximal end direction. The spiral fin 112 is fixed to the tube main body 110 by bonding or welding, or formed as one unitary piece with the tube main body 110, and radially protrudes from the external circumferential surface of the tube main body 110. The spiral fin 112 may be solid or hollow, or may be filled with fluid. The spiral fin 112 may be deformable such that the spiral fin 112 is reduced to easily pass through a narrow body cavity when the spiral fin advances inside the narrow body cavity and the spiral fin 112 has an enlarged shape when the spiral fin 112 performs a desired rotation advance after passing through the narrow body cavity. The spiral fin 112 is formed of, for example, polyurethane, TPE, silicone, TFE, medical grade stainless steel, tantalum, titanium, or nickel-titanium alloy or the like.

Figure 3:
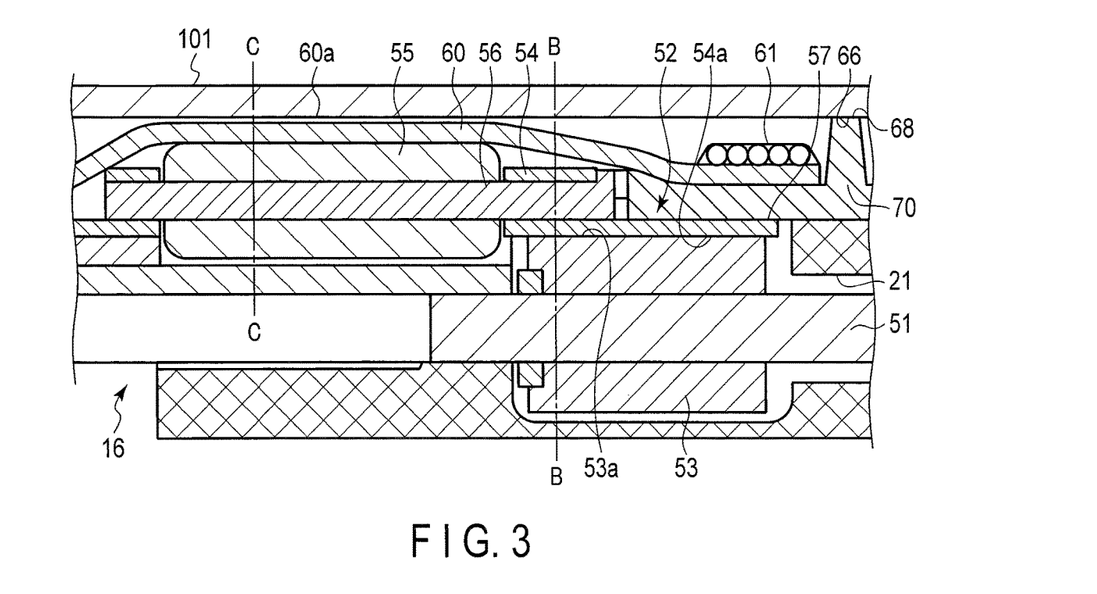
FIG. 3 is a cross-sectional view illustrating a drive unit provided in an insertion section of an endoscope main body, and configured to rotation-drive a tube of the rotation unit.
Figure 4:
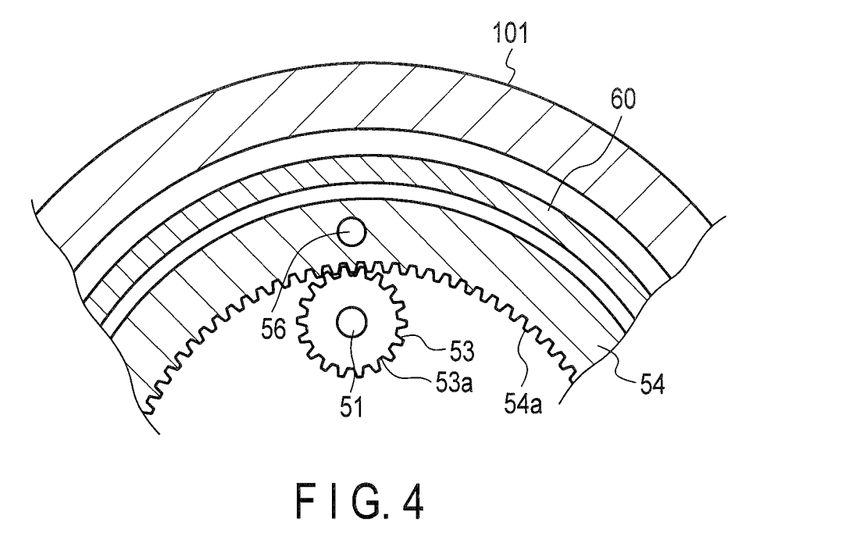
FIG. 4 is a cross-sectional view taken along line B-B of FIG. 3.

Next, the drive unit 50 to rotation-drive the tube 101 of the rotation unit 100 will be explained. FIG. 3 is a cross-sectional view illustrating the drive unit 50 provided in the insertion section 16 of the endoscope 11. FIG. 4 is a cross-sectional view taken along line B-B of FIG. 3. The drive unit 50 includes the drive shaft 51 and a gearbox 52. The gear box 52 includes a rotary gear 53, an internal gear 54, and a drive roller 55.

As illustrated in FIG. 1, the proximal end of the drive shaft 51 is connected with the rotary shaft of the motor main body 41. The drive shaft 51 is arranged in the channel 21 extending inside the insertion section 16. The drive shaft 51 may have, for example, a multi-layer structure in which metal wires that are woven in a cylindrical net shape are superimposed, or may be formed of multi-layered wires in which clockwise wires and counterclockwise wires are superimposed, and has rotation followability to the motor main body 41 and flexibility.

The distal end of the drive shaft 51 is provided with the rotary gear 53 of the gear box 52. The drive shaft 51 rotates the rotary gear 53, when a rotational force around the longitudinal axis is applied to the proximal end of the drive shaft 51. External teeth 53a of the rotary gear 53 are meshed with internal teeth 54a of the internal gear 54 provided on the external circumference of the insertion section 16. A shaft 56 of the drive roller 55 is attached to the internal gear 54. Accordingly, the drive force from the motor main body 41 of the drive source 40 is transmitted from the drive shaft 51, to rotation-drive the rotary gear 53, the internal gear 54, and the drive roller 55 of the gear box 52.

The internal gear 54 and the drive roller 55 are arranged to be shifted from each other in the longitudinal axis direction. With the structure, a space is formed on the external circumferential surface of the internal gear 54 in a range not exceeding the height of the drive roller 55. A bearing portion 57 is provided in the space in the present embodiment. The bearing portion 57 is provided on a base member 70, and serves as an opening portion that is slidably fitted on the external circumferential surface of the proximal end portion of the internal gear 54. In other words, in the longitudinal axis direction of the endoscope 11, the bearing portion 70 is arranged to be superimposed on the mesh portion between the external teeth 53a of the rotary gear 53 and the internal teeth 54a of the internal gear 54.

The internal gear 54 and the drive roller 55 are covered with a cover 60 at the external circumferential surface of the insertion section 16. The cover 60 is provided with a radial protruding portion 60a formed on its external surface by covering the drive roller 55. The cover 60 is a waterproof sheet member providing a barrier or a seal to protect the internal gear 54, the drive roller 55, and other members of the endoscope 11 arranged inside thereof. The cover 60 maintains watertightness of the inside of the endoscope 11 (insertion section 16), and prevents infiltration of water or other fluids. The cover 60 is fixed to the external circumferential surface of the insertion section 16 (base member 70) with a cover fixing member 61. Specifically, the cover 60 is bonded by spool bonding with the cover fixing member 61.

Figure 5:
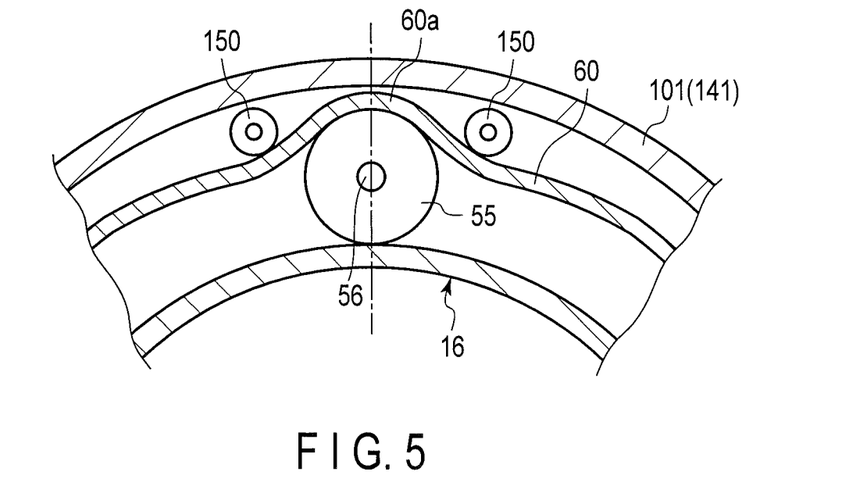
FIG. 5 is a cross-sectional view taken along line C-C of FIG. 3.

FIG. 5 is a cross-sectional view taken along line C-C of FIG. 3. As described above, the external circumferential surface of the drive roller 55 of the drive unit 50 is covered with the cover 60 outside the insertion section 16 in the radial direction. Outside the cover 60 in the radial direction, rollers 150 of the connector 120 described later are arranged one by one with the protruding portion 60a interposed therebetween, to abut against the external circumferential surface of the cover 60. The rollers 150 also abut against the internal circumferential surface of a release button main body 140 of the connector 120 of the tube 101 described later, outside the insertion section 16 in the radial direction.

When the drive unit 50 is driven, the drive force from the drive source 40 is transmitted to the drive roller 55, via the drive shaft 51, the rotary gear 53 and the internal gear 54 of the gearbox 52. In this manner, the drive roller 55 is rotated around the rotational axis A1. The drive roller 55 and the rollers 150 rotate on the cover 60 to reduce friction caused by the cover 60. Because the cover 60 is fixed to the external circumferential surface of the insertion section 16, the cover 60 is not rotated with respect to the insertion section 16. By contrast, the two rollers 150 maintain the drive roller 55 between the rollers 150, and thereby the driver roller 55 transmits the rotational movement of the internal gear 54 to the tube 101 beyond the cover 60. Thus, the drive force from the drive source 40 is transmitted from the drive unit 50 to the rotation unit 100, and the rotation unit 100 is rotation-driven around the rotational axis A1. For example, when inspection of the small intestine or the large intestine is performed, the rotation unit 100 advances while pressing the folds of the small intestinal wall and the large intestinal wall abutting against the spiral fin 112 of the rotating tube main body 110 toward the proximal end, to assist the insertion of the insertion section 16.

The internal circumferential surface of the tube 101 is provided with a bearing surface 66 that is located on the proximal end side beyond the drive roller 55 transmitting the drive force as illustrated in FIG. 3, and engaged with a bearing surface 68 provided on the external circumferential surface of the base member 70. The bearing surfaces 66 and 68 are circumferential surfaces. An internal diameter of the bearing surface 66 is formed slightly larger than the external diameter of the bearing surface 68 such that the bearing surface 66 is slidable with respect to the bearing surface 68 with rotation of the tube 101 with respect to the insertion section 16. Specifically, the bearing surfaces 66 and 68 function as a radial movement restricting mechanism restricting movement of the tube 101 in the radial direction of the insertion section 16.

Figure 6:
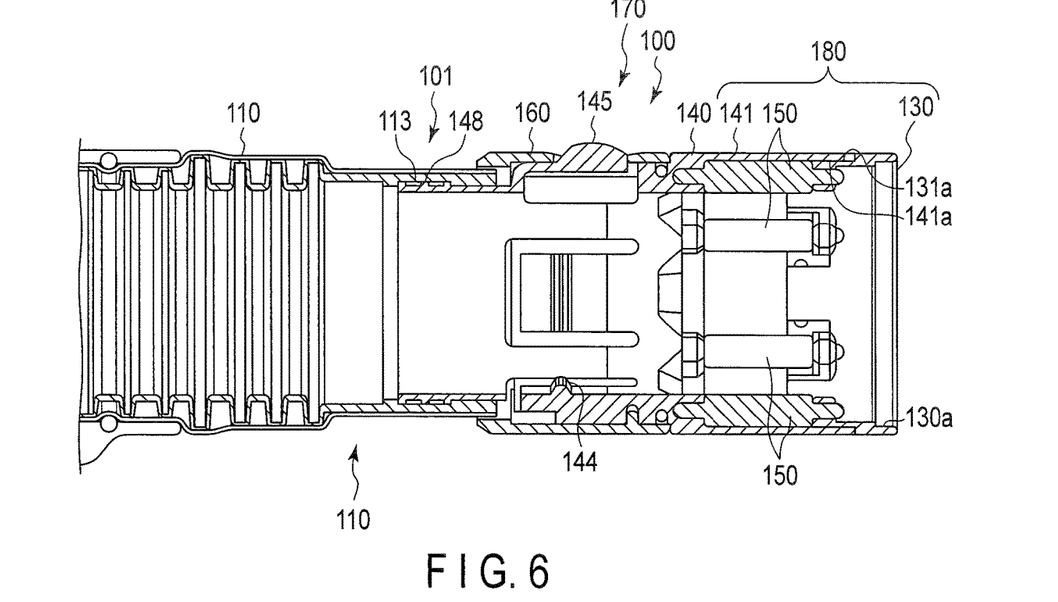
FIG. 6 is a cross-sectional view illustrating the tube of the rotation unit.

Next, the connector 120 of the rotation unit 100 will be explained. FIG. 6 is a cross-sectional view illustrating the tube 101 of the rotation unit 100. The connector 120 being a constituent element of the tube 101 includes an annular proximal end sleeve 130, the release button main body 140, and the rollers 150 described above. The proximal end sleeve 130 is engaged with the release button main body 140. The proximal end sleeve 130 and the release button main body 140 rotatably hold the rollers 150. The release button main body 140 is also engaged with a locking collar 160 that is slidable in the longitudinal axis direction of the tube 101.

Figure 7:
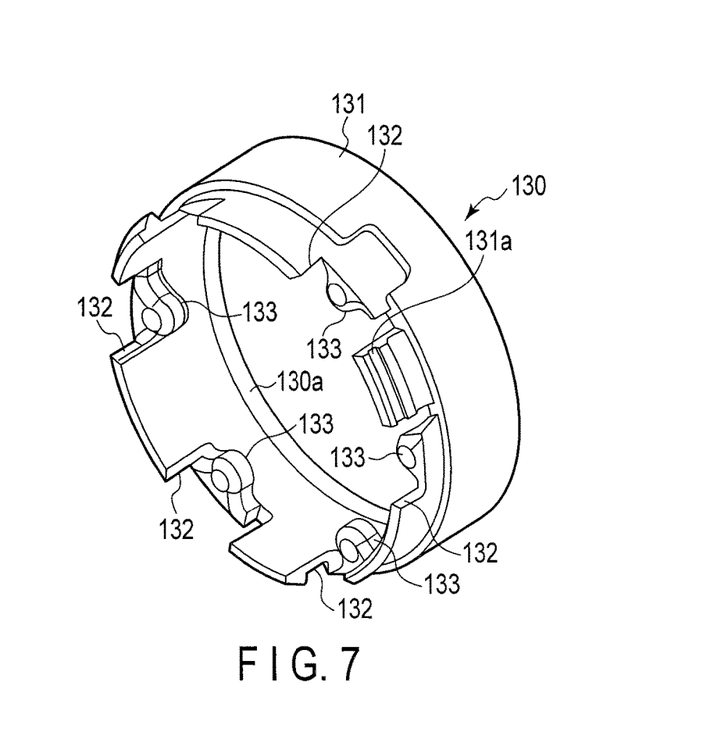
FIG. 7 is a perspective view illustrating a proximal end sleeve of a connector.
Figure 8:
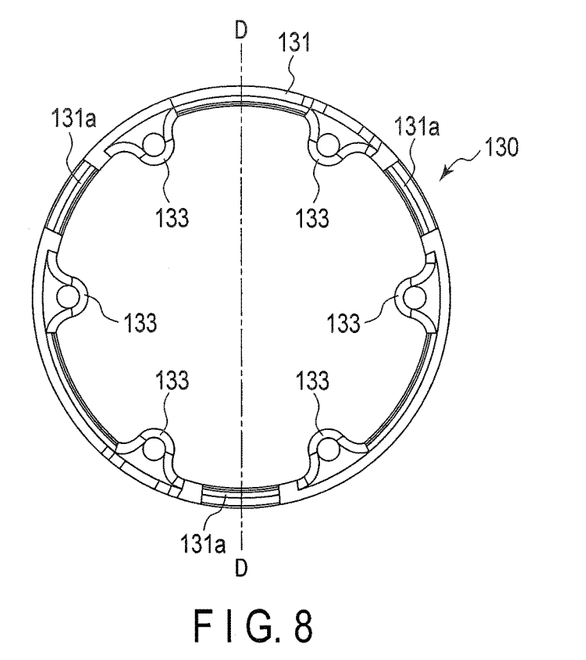
FIG. 8 is a diagram of the proximal end sleeve of the connector as viewed from a distal end side.
Figure 9:
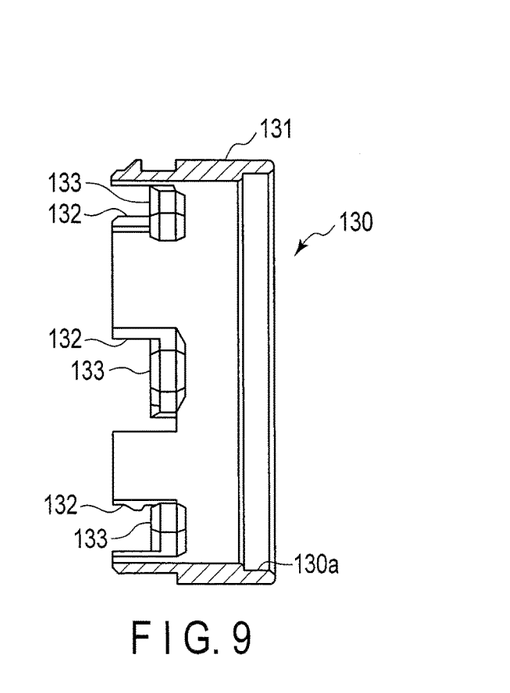
FIG. 9 is a cross-sectional view taken along line D-D of FIG. 8.

FIG. 7 to FIG. 9 are a perspective view of the proximal end sleeve 130, a front view thereof as viewed from the distal end side, and a cross-sectional view thereof taken along line D-D of FIG. 8, respectively. The proximal end sleeve 130 includes six cutout portions 132 formed in the distal end portion of the cylindrical wall 131, and six roller holding portions 133 arranged in the respective cutout portions 132. The roller holding portions 133 radially protrude from the internal circumferential surface of the proximal end sleeve 130, to hold the rollers 150 substantially parallel with the longitudinal axis direction of the insertion section 16 when the tube 101 is attached onto the insertion section 16. In the present embodiment, one end portions of the six rollers 150 are held to be rotatable around the axis by the corresponding roller holding portions 133, respectively. Three engaging portions 131a, each having an uneven shape on the external surface thereof, are formed on the distal end side of the cylindrical wall 131 of the proximal end sleeve 130. These engaging portions 131a are engaged with respective corresponding engaging portions 141a formed on the internal circumference of a large-diameter portion 141 of the release button main body 140 described later. A large-diameter internal circumferential surface 130a provided on the internal circumference of the proximal end sleeve 130 on the proximal end side has a structure corresponding to the bearing surface 66 (see FIG. 3) described above, and slidably fitted with a surface of the insertion section corresponding to the bearing surface 68.

Figure 10:
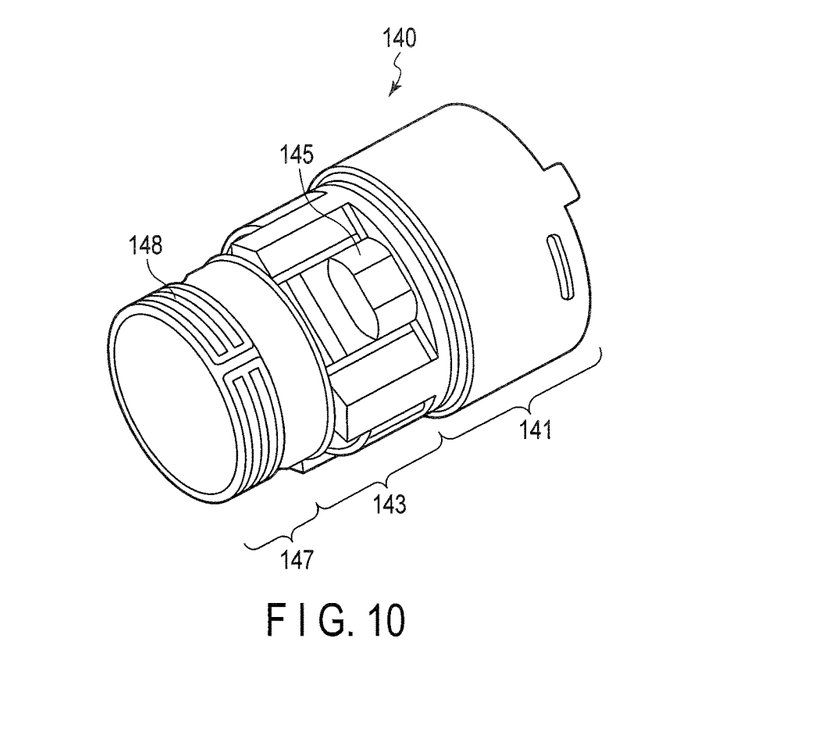
FIG. 10 is a perspective view illustrating a release button main body of the connector.
Figure 11:
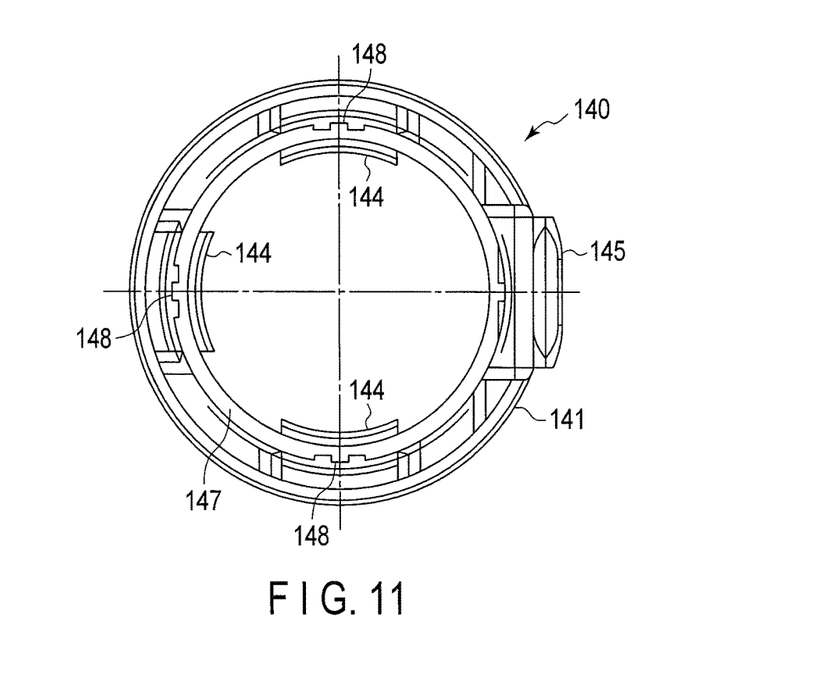
FIG. 11 is a diagram of the release button main body of the connector as viewed from the distal end side.
Figure 12:
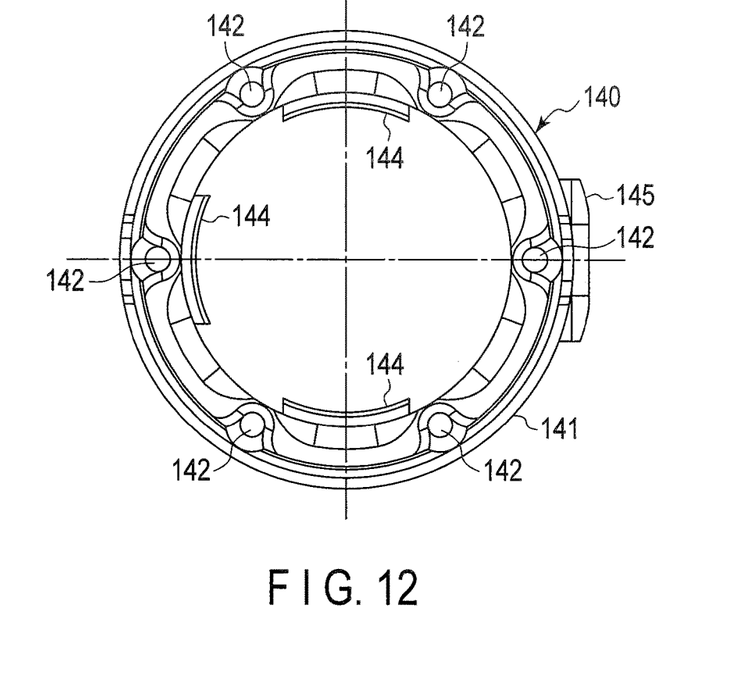
FIG. 12 is a diagram of the release button main body of the connector as viewed from a proximal end side.

FIG. 10 to FIG. 12 are a perspective view of the release button main body 140, a front view thereof as viewed from the distal end side, and a back view thereof as viewed from the proximal end side, respectively. The release button main body 140 includes the large-diameter portion 141 on the proximal end side, a medium-diameter portion 143 in the middle, and a small-diameter portion 147 on the distal end side. The large-diameter portion 141 has an external diameter larger than the external diameter of the medium-diameter portion 143, and the external diameter of the medium-diameter portion 143 is larger than the external diameter of the small-diameter portion 147. The large-diameter portion 141 has an internal diameter larger than internal diameters of the medium-diameter portion 143 and the small-diameter portion 147, and the internal diameters of the medium-diameter portion 143 and the small-diameter portion 147 are substantially equal. In particular, the internal circumferential surfaces of the large-diameter portion 141, the medium-diameter portion 143, and the small-diameter portion 147 form part of the lumen 111 in the tube 101, and have a shape running along the shape of the external circumferential surface of the insertion section 16 inserted through the lumen 111.

The large-diameter portion 141 is provided with six roller holding portions 142 to hold the other end portions of the six rollers 150. The roller holding portions 142 hold the respective rollers 150 rotatably in the axial direction, together with the roller holding portions 133 of the proximal end sleeve 130. The large-diameter portion 141 forms a connecting mechanism 180 to rotatably attach the tube 101 to the insertion section 16, together with the proximal end sleeve 130 and the rollers 150. As described above, the connecting mechanism 180 is configured to be engaged with the protruding portion 60a formed on the cover 60 and receive the drive force from the drive unit 50. Specifically, the connecting mechanism 180 is provided on the tube 101, receives the drive force from the drive unit 50, and is rotated with respect to the insertion section 16 inserted through the lumen 111 of the tube main body 110.

The medium-diameter portion 143 is provided with one or a plurality of pawls (convex portions) 144 radially protruding from an internal surface thereof. The pawls 144 are engaged with grooves (concave portions) 59 arranged in the insertion section 16 described later, to form a locking mechanism 170. The medium-diameter portion is also provided with a release button 145 radially protruding from an external surface thereof. As illustrated in FIG. 6, the release button 145 is supported by the medium-diameter portion 143 in a cantilever manner. This structure enables the release button 145 to move in the substantially radial direction when the user pushes the release button 145 from above or slides the locking collar 160 to a position on the release button 145. The release button 145 also forms the locking mechanism 170 by being engaged with an opening 161 of the locking collar 160 described later.

Engaging portions 148 are formed on the external circumferential surface of the small-diameter portion 147. The engaging portions 148 are attached to corresponding engaging portions 113 formed on the internal circumferential surface of the proximal end portion of the tube main body 110.

Figure 13:
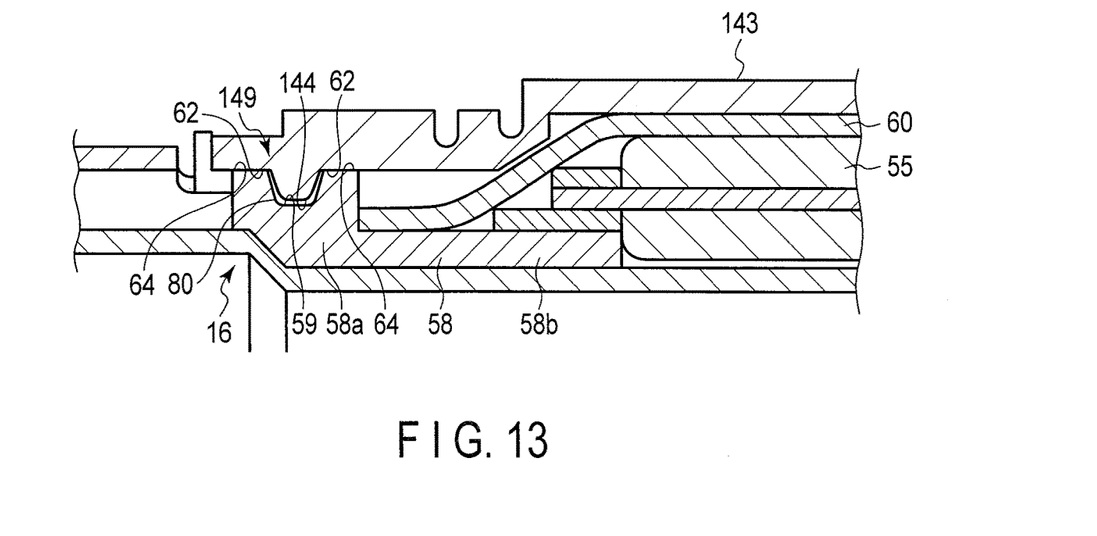
FIG. 13 is a perspective view illustrating a locking collar of the rotation unit.

Next, an attached state between the insertion section 16 of the endoscope 11 and the tube 101 of the rotation unit 100 will be explained. FIG. 13 is a cross-sectional view illustrating the attached state between the insertion section 16 and the tube 101. In the insertion section 16, the distal end side of the drive roller 55 is provided with an annular receiving member 58 to receive the pawls 144 of the release button main body 140 of the connector 120. The receiving member 58 is part of the gear box 52, and serves as a fixed part that is not rotated with respect to the insertion section 16. The receiving member 58 is arranged on the external circumferential surface of the insertion section 16, and includes a distal end side portion 58a having a larger radial height, and a proximal end side portion 58b having a radial height smaller than that of the distal end side portion 58a. The distal end side portion 58a is provided with grooves 59 recessed in the radial direction and extending along the circumferential direction of the external circumferential surface of the insertion section 16. The distal end side of the cover 60 is fixed to the proximal end side portion 58b.

As described above, the tube 101 of the rotation unit 100 includes one or a plurality of pawls 144 provided in the medium-diameter portion 143 of the release button main body 140. Specifically, the pawls 144 are arranged on the distal end side beyond the proximal end sleeve 130, the rollers 150, and the large-diameter portion 141 of the release button main body 140 that form the connecting mechanism 180 in the tube 101. The pawls 144 protrude from the internal surface of the medium-diameter portion 143 in the internal diameter direction, and are engaged with the grooves 59 formed in the receiving member 58. The pawls 144 are engaged with the grooves 59, to restrict movement of the tube 101 with respect to the insertion section 16 along the longitudinal axis direction of the tube 101 (or the insertion section 16). In addition, when the pawls 144 are engaged with the grooves 59, the pawls 144 move along the circumferential direction of the external circumferential surface of the insertion section 16, with rotation of the tube 101. The internal circumferential surface (internal circumferential surface of the medium-diameter portion 143) of the tube 101 is provided with bearing surfaces 62 on the distal end side and the proximal end side of the pawls 144, and the external circumferential surface (external circumferential surface of the receiving member 58) of the insertion section 16 is provided with bearing surfaces 64 on the distal end side and the proximal end side of the grooves 59. The bearing surfaces 64 are formed of circumferential surfaces, and the bearing surfaces 62 are arc-shaped surfaces with a curvature radius that is set slightly larger than the curvature radius of the bearing surfaces 64 such that the bearing surfaces 62 are slidable with respect to the bearing surfaces 64. The bearing surfaces 62 and the bearing surfaces 64 are configured to be mutually opposed and abut against each other when the tube 101 is inserted into the insertion section 16 and the pawls 144 are engaged with the grooves 59. This structure restricts movement of the tube 101 in the radial direction of the insertion section 16. With rotation of the tube 101, the bearing surfaces 62 relatively move with respect to the bearing surfaces 64.

In the present embodiment, the position in which the grooves 59 formed in the receiving member 58 in the insertion section 16 are engaged with the pawls 144 formed in the medium-diameter portion 143 of the release button main body 140 in the connector 120 is located on a more distal end side in the longitudinal axis direction than the position in which the cover 60 is provided. The grooves 59 and the pawls 144 in the engaged state include a bearing mechanism 149 formed of the bearing surfaces 62 and the bearing surfaces 64. The bearing mechanism 149 is also provided on a more distal end side than a position in which the tube 101 receives the drive force from the drive unit 50 at the connecting mechanism 180. The bearing mechanism 149 suppresses eccentricity of the rotation center from the central axis A1 of the insertion section 16 when the tube 101 is attached to the insertion section 16 and rotated around the longitudinal axis.

Figure 14:
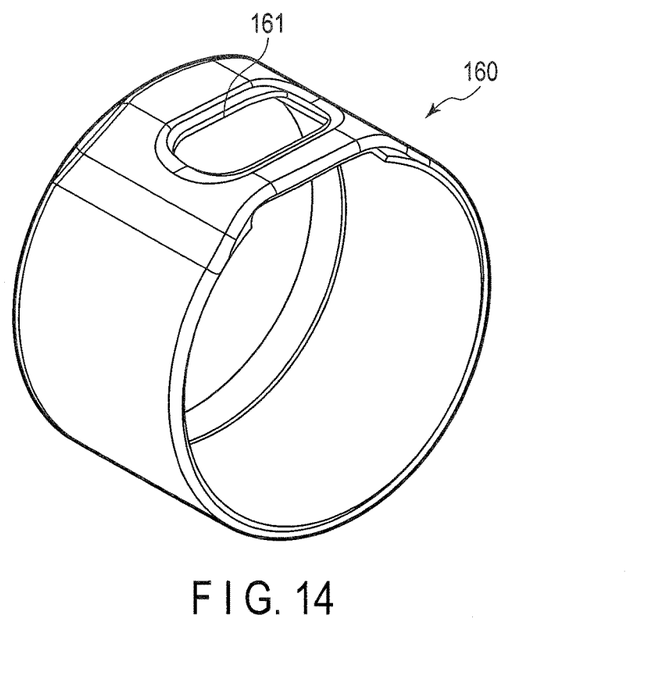
FIG. 14 is a cross-sectional view illustrating an attached state between the insertion section of the endoscope and the tube of the rotation unit.

Next, the locking collar 160 will be explained. FIG. 14 is a perspective view illustrating the locking collar 160 of the rotation unit 100. The locking collar 160 is a hollow annular member, and configured with a size substantially being fitted onto the size of the medium-diameter portion 143 of the release button main body 140. The locking collar 160 is provided with the opening 161 to be engaged with the release button 145 of the release button main body 140.

Next, a process to attach the rotation unit 100 to the endoscope system 10 will be explained.

The user inserts the tube 101 of the rotation unit 100 into the insertion section 16 from the distal end side of the insertion section 16 of the endoscope 11. Thereafter, as illustrated in FIG. 13, the grooves 59 formed in the receiving member 58 in the insertion section 16 are engaged with the pawls 144 formed in the medium-diameter portion 143 of the release button main body 140. As illustrated in FIG. 5, the rollers 150 fixed to the large-diameter portion 141 of the release button main body 140 abut against the protruding portion 60a formed by abutment of the drive roller 55 against the cover 60. Specifically, the rollers 150 abut against the drive roller 55 of the drive unit 50 arranged in the insertion section 16 via the cover 60. The locking collar 160 is engaged with the release button main body 140 of the connector 120, in the state where the pawls 144 of the connector 120 are engaged with the grooves 59 of the receiving member 58.

Figure 15:
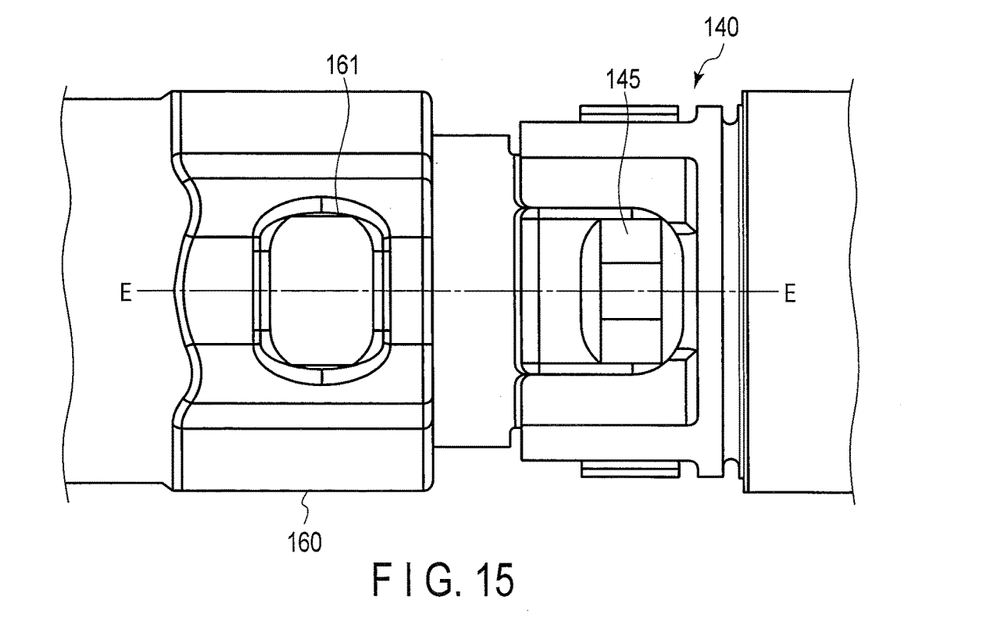
FIG. 15 is a top view illustrating the release button main body and the locking collar in an unlocked position.
Figure 16:
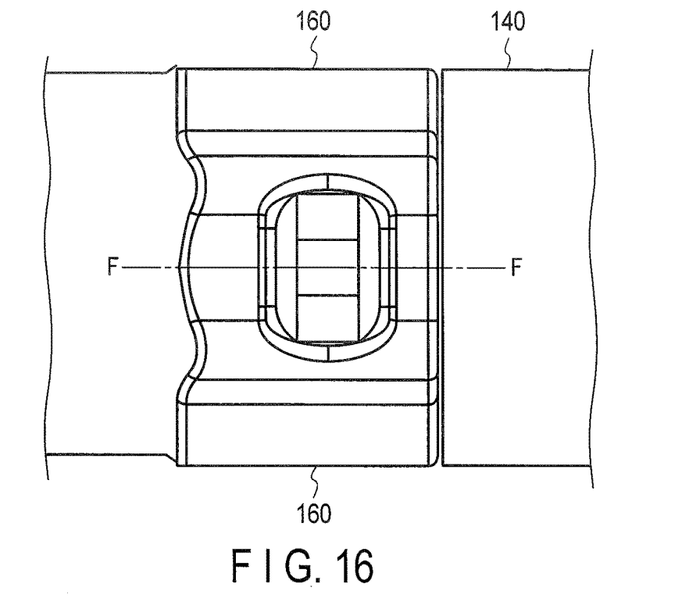
FIG. 16 is a top view illustrating the release button main body and the locking collar in a locked position.
Figure 17:
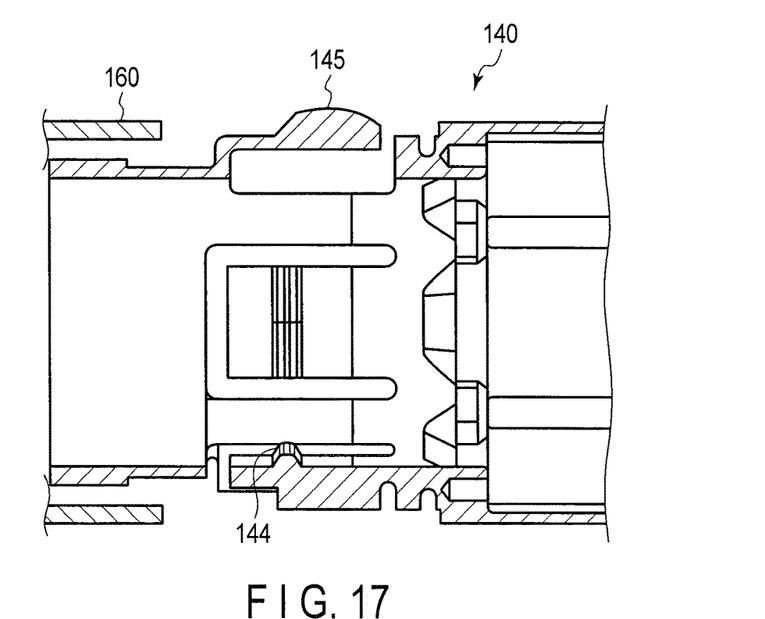
FIG. 17 is a cross-sectional view taken along line E-E in FIG. 15.
Figure 18:
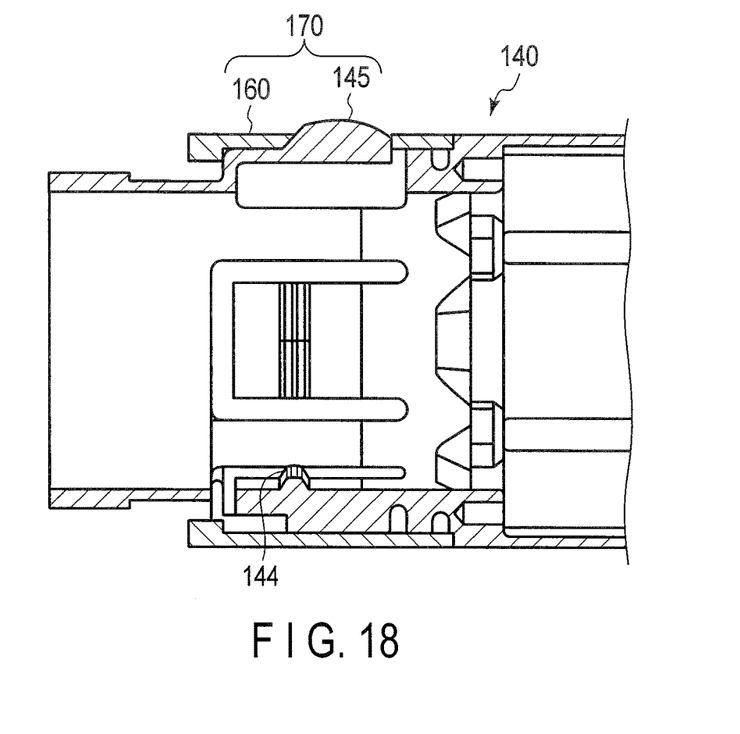
FIG. 18 is a cross-sectional view taken along line F-F in FIG. 16.
Figure 19:
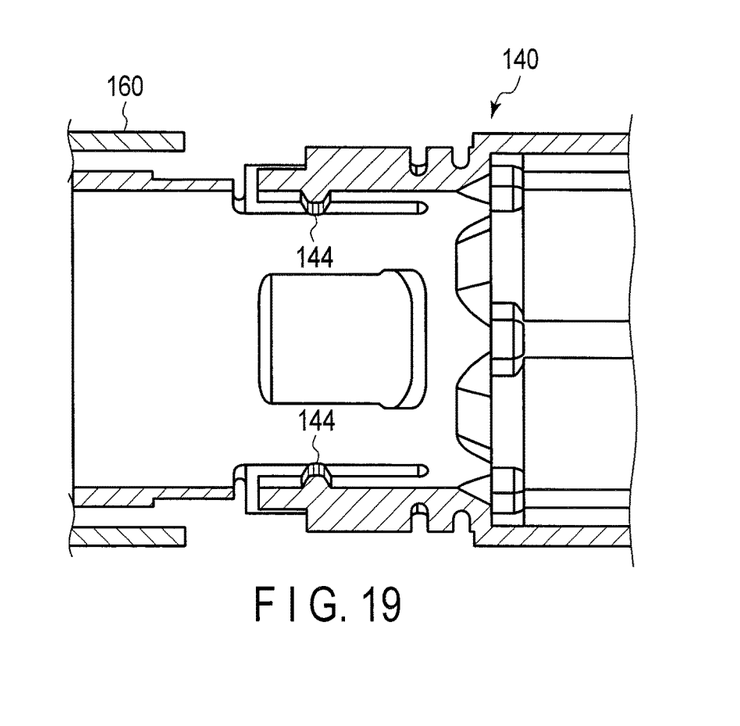
FIG. 19 is a cross-sectional view in a direction orthogonal to the cross section illustrated in FIG. 17.
Figure 20:
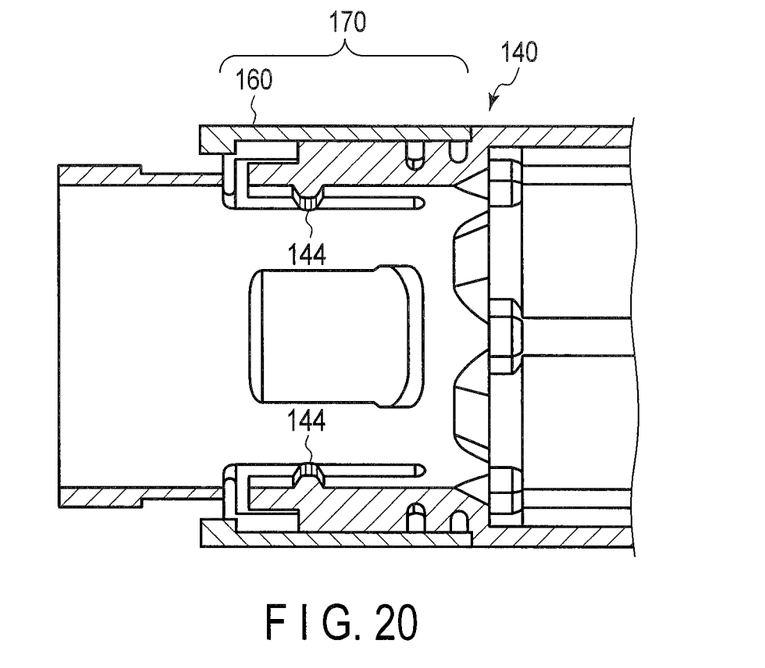
FIG. 20 is a cross-sectional view in a direction orthogonal to the cross section illustrated in FIG. 18.

FIG. 15 and FIG. 16 are top views of the release button main body 140 and the locking collar 160 in an unlocked position and a locked position, respectively. FIG. 17 and FIG. 18 are a cross-sectional view taken along line E-E of FIG. 14, and a cross-sectional view taken along line F-F of FIG. 15, respectively. FIG. 19 and FIG. 20 are cross-sectional views in a direction orthogonal to the cross sections illustrated in FIG. 17 and FIG. 18, respectively. Specifically, FIG. 19 and FIG. 20 illustrate cross sections parallel with the central axis A1 and perpendicular to the cross sections of FIG. 17 and FIG. 18, respectively. The rocking collar 160 is slidably attached to the external circumferential surface of the tube 101 such that the release button 145 of the medium-diameter portion 143 of the release button main body 140 is aligned with the opening 161 of the locking collar 160 in the radial direction.

In the unlocked position illustrated in FIG. 15, FIG. 17, and FIG. 19, the locking collar 160 is located on a more distal end side, for example, the small-diameter portion 147, than the medium-diameter portion 143 of the release button main body 140. In the state in which the pawls 144 are engaged with the grooves 59, the locking collar 160 is slid from the unlocked position to the medium-diameter portion 143 of the release button main body 140. The opening 161 of the locking collar 160 is engaged with the release button 145 provided on the medium-diameter portion 143 (locked position). Because the release button 145 is in a cantilever manner, when the locking collar 160 is moved onto the release button 145, the release button 145 is slightly flexed to be pushed down in the radial direction from the medium-diameter portion 143, and fitted and fixed into the opening 161. Thus, the pawls 144 of the connector 120 and the grooves 59 of the receiving member 58 are pressed from the upper surface, and it prevents the pawls 144 from coming off the grooves 59. As a result, it prevents the tube 101 from moving in the longitudinal axis direction of the tube 101 (or the insertion section 16) with respect to the insertion section 16. In addition, because the bearing surfaces 62 and 64 are provided on the distal end side of the drive roller 55, and the bearing surfaces 66 and 68 are provided on the proximal end side of the drive roller 55, the bearing surfaces further suppress eccentricity of the rotation center that causes shaking when the tube 101 is rotated around the longitudinal axis. Thus, the locking mechanism 170 includes both an axial movement restricting mechanism achieved by engagement of the pawls 144 and the grooves 59, and a radial movement restricting mechanism achieved by slidable fitting of the bearing surfaces 62 and the bearing surfaces 64.

Next, a process of removing the rotation unit 100 from the endoscope system 10 will be explained.

When the rotation unit 100 is removed from the endoscope system 10, the user pushes in the release button 145. Thereby, the release button 145 is moved inward in the radial direction, and detached from the opening 161. Thereafter, by sliding the locking collar 160 again toward the distal end side, the locking collar 160 is returned to the unlocked position, and restriction of movement of the pawls 144 in the radial direction is removed. In addition, the tube 101 is moved toward the distal end side with respect to the insertion section 16. In this manner, the pawls 144 are raised up and disengaged from the grooves 59, and the tube 101 is removed from the insertion section 16.

Thus, the locking mechanism 170 includes the locking collar 160 configured to be movable in the longitudinal axis direction and move between the locked position in which the locking collar 160 is engaged with the pawls 144 to restrict movement of the pawls 144 outward in the radial direction of the tube 101, and the unlocked position in which the locking collar 160 is not engaged with the pawls 144, in addition to the pawls 144 provided on a more distal end side than the connecting mechanism 180 in the tube 101 and engaged with the insertion section 16 to restrict movement of the tube 101 along the longitudinal axis with respect to the endoscope 11. Because the locking mechanism 170 includes convex portions (pawls 144) and the concave portions (grooves 59) to restrict movement of the rotation unit 100 in the longitudinal axis direction, and the bearing surfaces 62 and 64 to restrict movement in the radial direction, the rotation unit 100 can be securely fixed to the insertion section 16.

When the tube 101 is attached to the endoscope 11, for example, in the case where pawls provided on the rotation unit side are engaged with a flange located on a more proximal end side than the cover on the endoscope side to fix the tube 101 to the insertion section 16 in the axial direction, the pawls are required to move across the cover to be fixed. Because the pawls protrude inward in the radial direction of the tube 101, sufficient attention is paid to the positions of the protruding portions of the cover and the pawls in performing attachment; otherwise the pawls may catch the cover and break the cover.

By contrast, in the present embodiment, in the state where the rotation unit 100 is attached to the endoscope 11, the pawls 144 provided on the rotation unit side are arranged on a more distal end side in the longitudinal axis direction than the protruding portion 60a of the cover 60 covering the drive roller 55 of the drive unit 50 provided on the endoscope side. Thus, the pawls 144 do not pass over the cover 60 when the tube 101 is attached to the insertion section 16. This structure prevents the pawls 144 from catching the cover 60 and breaking the cover in attachment, and securely prevents infiltration of water or another fluid into the insertion section 16.

Figure 21:
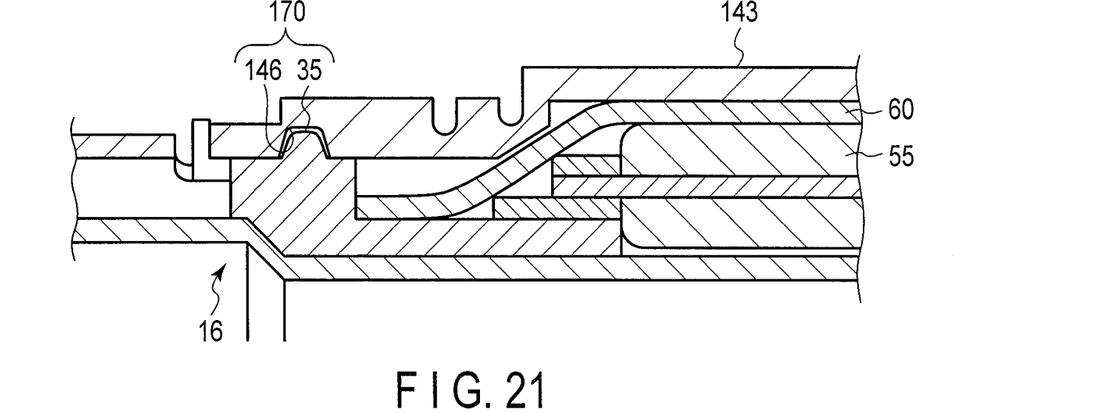
FIG. 21 is a cross-sectional view illustrating an attached state between the insertion section of the endoscope and the tube of the rotation unit.

The pawls (first engaging portion) 144 provided on the tube 101 and the grooves (second engaging portion) 59 provided on the endoscope 11 have been explained above as the locking mechanism 170 restricting movement of the tube 101 in the longitudinal axis direction, but the movement restricting mechanism in the longitudinal axis direction is not limited thereto. For example, as illustrated in FIG. 21, the movement restricting mechanism may be annular concave portions 146 (first engaging portion) provided in the internal circumferential surface of the tube 101 and one or a plurality of convex portions (second engaging portion) 35 provided on the external circumferential surface of the insertion section 16 on a more distal end side than the cover 60. It also prevents breakage of the cover, because the convex portions 135 do not catch the cover 60.

Thus, the present embodiment provides the rotation unit 100 without a fear of breaking the cover 60 when the rotation unit 100 is attached to the endoscope 11, the endoscope 11 to which the rotation unit 100 is attached, and the endoscope apparatus 1 including them.

In the present embodiment, the internal circumferential surface forming the lumen 111 has a shape running along the shape of the external circumferential surface of the insertion section 16 inserted therein. In addition, the internal circumferential surface of each of the pawls 144 has a shape running along the shape of the grooves 59 provided in the external circumferential surface of the insertion section 16. When the tube 101 is attached to the insertion section 16, the bearing mechanism is formed between the internal circumferential surface and the external circumferential surface. This structure prevents the rotation center from becoming eccentric when the tube 101 is rotated around the longitudinal axis.

In addition, in the case where the drive roller is arranged on the internal gear rotating around the endoscope insertion axis, it has the problem that the external diameter of the insertion section is increased in comparison with an ordinary insertion section of an endoscope to which no insertion assistant rotation unit is attached. To improve the problem, for example, it is conceived that the roller is arranged in a position shifted in the axial direction from the portion serving as a tooth surface of the internal gear, for example. However, the structure of arranging the tooth surface of the internal gear and the roller to be simply shifted from each other in the axial direction increases the length of the hard portion in the insertion section, and may have unfavorable influence on flexibility of the insertion section. Thus, the conventional art fails to increase in the external diameter and the length of the hard portion of the insertion section.

By contrast, in the present embodiment, part of the external circumferential surface of the internal gear 54 is formed as the bearing portion 57 to align the rotational axis of the internal gear 54 with the rotational base axis. Because the internal gear 54 and the drive roller 55 are arranged to be shifted from each other in the axial direction, the external diameter of the insertion section 16 is not unnecessarily increased. In addition, because the meshed portion of the external teeth 53a of the rotary gear 53 and the internal teeth 54a of the internal gear 54 is arranged to be superimposed on the bearing portion 57 in the longitudinal axis direction, this structure reduces the length of the hard portion in the portion to which the rotation unit 100 is attached in the insertion section 16.

The explanation described above takes the endoscope system 10 as the insertion apparatus to which the rotation unit 100 is attached, but the insertion apparatus is not limited to an endoscope. For example, the insertion apparatus may be an insertion apparatus to and from which a tube rotatable with respect to the insertion section is attachable and detachable, such as an operation manipulator. Accordingly, the introduction apparatus may be an apparatus including the rotation unit, and an insertion apparatus that is not limited to an endoscope to and from which the rotation unit is attachable and detachable.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An assist tool attachable to an insertion section of an insertion apparatus, the assist tool comprising:
   a tube including a distal end portion and a proximal end portion, the tube including a longitudinal axis extending from the distal end portion to the proximal end portion, the tube being provided with a lumen through which the insertion section is insertable;
   a connecting mechanism provided in the tube to rotatably attach the tube to the insertion section, the connecting mechanism receiving a drive force and being rotated integrally with the tube with respect to the insertion section inserted through the lumen;
   a locking mechanism provided in the tube, the locking mechanism being positioned distally relative to the connecting mechanism, the locking mechanism including one of a convex portion and a concave portion to be engaged with an other of the convex portion and the concave portion arranged on the insertion section to restrict movement of the tube along the longitudinal axis with respect to the insertion section; and
   first and second bearing surfaces arranged distally and proximally, respectively, to the one of the convex portion and the concave portion of the locking mechanism, the first and second bearing surfaces engaging corresponding first and second bearing surfaces arranged on the insertion section.

2. The assist tool according to claim 1, wherein tube having an internal circumferential surface forming the lumen, the internal circumferential surface having a shape corresponding to a shape of an external circumferential surface of the insertion section such that the internal circumferential surface is slidable relative to the external circumferential surface when the tube is attached to the insertion section.

3. The assist tool according to claim 2, wherein at least a portion of the internal circumferential surface of the tube is fitted onto the external circumferential surface of the insertion section proximally to a portion of the connecting mechanism in which the drive force is received.

4. The assist tool according to claim 1, wherein the locking mechanism includes the convex portion and the convex portion comprises at least one pawl protruding from the lumen of the tube in an internal diameter direction.

5. The assist tool according to claim 4, wherein an internal circumferential surface of the at least one pawl has a convex shape for engagement with a concave shape of the external circumferential surface of the insertion section, and the internal circumferential surface is slidably fitted onto the external circumferential surface when the tube is attached to the insertion section.

6. The assist tool according to claim 1, wherein the locking mechanism includes an annular member formed to slide in a direction of the longitudinal axis, the annular member being configured to move between;
   a locked position in which the annular member is engaged with the one of the convex portion and the concave portion to restrict movement of the one of the convex portion and the concave portion outward in a radial direction of the tube, and
   an unlocked position in which the annular member is not engaged with the one of the convex portion and the concave portion.

7. An insertion apparatus for use with the assist tool according to claim 1, the insertion apparatus comprising:
   the other of the concave portion the convex portion arranged an external circumferential surface of the insertion section and fitted with the one of the convex portion and the concave portion of the locking mechanism such that the one of the convex portion and the concave portion of the locking mechanism moves along the external circumferential surface of the insertion section with rotation of the tube; and
   the corresponding first and second bearing surfaces arranged on the external circumferential surface of the insertion section.

8. An insertion apparatus for use with the assist tool according to claim 1, the insertion apparatus comprising:
   a roller provided inside the insertion section and rotated by transmission of the drive force; and
   a cover covering the roller to form a protruding portion on an external surface of the cover, the cover being configured to maintain an inside of the insertion section watertight against an external environment,
   wherein the protruding portion is configured to engage the connecting mechanism and transfer the drive force to the connecting mechanism to rotate the connecting mechanism and the tube with respect to the insertion section.

9. An introduction apparatus comprising:
   the assist tool according to claim 1;
   the insertion apparatus including the other of the concave portion the convex portion arranged an external circumferential surface of the insertion section, the other of the concave portion and the convex portion of the insertion apparatus being slidably engaged with the one of the convex portion and the concave portion of the locking mechanism such that the one of the convex portion and the concave portion of the locking mechanism moves along the external circumferential surface of the insertion section with rotation of the tube; and
   the corresponding first and second bearing surfaces arranged on the external circumferential surface of the insertion section.

10. An insertion apparatus for use with the assist tool according to claim 1, the insertion apparatus comprising:
    an internal gear that is rotated and driven to transmit the drive force to the connecting mechanism; and
    a base member including a bearing portion fitted on an external circumference of an proximal end portion of the internal gear and serving as a bearing of the internal gear.

* * * * *